United States Patent [19]
Carling et al.

[11] Patent Number: 5,939,436
[45] Date of Patent: Aug. 17, 1999

[54] FIVE-MEMBERED HETEROAROMATIC COMPOUNDS AS DOPAMINE RECEPTOR SUBTYPE LIGANDS

[75] Inventors: William Robert Carling, Bishops Stortford, United Kingdom; Paul David Leeson, Princeton, N.J.; Kevin William Moore, Buntingford, United Kingdom

[73] Assignee: Merck Sharp & Dohme Ltd., Hoddesdon, United Kingdom

[21] Appl. No.: 08/875,059

[22] PCT Filed: Feb. 13, 1997

[86] PCT No.: PCT/EP97/00678
§ 371 Date: Jun. 25, 1997
§ 102(e) Date: Jun. 25, 1997

[87] PCT Pub. No.: WO96/21660
PCT Pub. Date: Jul. 18, 1996

[30] Foreign Application Priority Data

Jan. 12, 1995 [GB] United Kingdom .................... 9500580

[51] Int. Cl.⁶ ........................ A61K 31/445; C07D 401/04
[52] U.S. Cl. ........................... 514/326; 514/318; 546/193; 546/194; 546/208; 546/209; 546/211
[58] Field of Search ............................. 546/211; 514/326

[56] References Cited

U.S. PATENT DOCUMENTS

5,227,486  7/1993  Merce-Vidal et al. .................. 544/295

FOREIGN PATENT DOCUMENTS

| WO 93/10742 | 6/1993 | WIPO . |
| WO 94/10162 | 5/1994 | WIPO . |
| WO 94/27994 | 12/1994 | WIPO . |
| WO 95/02591 | 1/1995 | WIPO . |
| WO 95/07904 | 3/1995 | WIPO . |

OTHER PUBLICATIONS

Cram and Hammond, "Organic Chemistry", McGraw–Hill Book Co., NY (1964) 2nd Ed. pp. 565–567.

*Primary Examiner*—Patricia L. Morris
*Attorney, Agent, or Firm*—Philippe L. Durette; Melvin Winokur

[57] ABSTRACT

A class of heteroaromatic compounds incorporating a substituted five-membered heteroaromatic nucleus which contains at least two nitrogen atoms are ligands for dopamine receptor subtypes within the body and are therefore useful in the treatment and/or prevention of disorders of the dopamine system, in particular schizophrenia and depression.

7 Claims, No Drawings

FIVE-MEMBERED HETEROAROMATIC COMPOUNDS AS DOPAMINE RECEPTOR SUBTYPE LIGANDS

This invention relates to a particular class of heterocyclic compounds which incorporate a substituted five-membered heteroaromatic nucleus containing at least two nitrogen atoms. More particularly, the invention concerns substituted pyrazole, imidazole, triazole and tetrazole derivatives which are ligands for dopamine receptor subtypes within the body, in particular the dopamine $D_4$ receptor subtype. They are therefore of use in the treatment and/or prevention of disorders of the dopamine system, including schizophrenia, depression, anxiety, nausea, Parkinson's disease, tardive dyskinesias and extrapyramidal side-effects associated with treatment by conventional neuroleptic agents, neuroleptic malignant syndrome, disorders of hypothalamic-pituitary function such as hyperprolactinaemia and amenorrhoea, and delusional disorders (cf. Catalano et al., *Biol. Psychiatry*, 1993, 34, 459).

Upper gastrointestinal tract motility is believed to be under the control of the dopamine system. The compounds according to the present invention may thus be of use in the prevention and/or treatment of gastrointestinal disorders, and the facilitation of gastric emptying.

Dependence-inducing agents such as cocaine and amphetamine have been shown to interact with the dopamine system. Compounds capable of counteracting this effect, including the compounds in accordance with the present invention, may accordingly be of value in the prevention or reduction of dependence on a dependence-inducing agent.

Dopamine is known to be a peripheral vasodilator; for example, it has been shown to exert a dilatory effect on the renal vascular bed. This implies that the compounds of the present invention may be beneficial in controlling vascular blood flow.

The localisation of dopamine receptor mRNA in rat heart and large vessels has been noted. This suggests a role for dopamine receptor ligands in controlling cardiovascular function, either by affecting cardiac and smooth muscle contractility or by modulating the secretion of vasoactive substances. The compounds according to the present invention may therefore be of assistance in the prevention and/or treatment of such conditions as hypertension and congestive heart failure.

By virtue of their activity as ligands for dopamine receptor subtypes within the body, the compounds in accordance with the present invention may also be of benefit in enhancing cognitive function, and in treating and/or preventing cognitive disorders including presenile and senile dementia (also known as Alzheimer's disease and senile dementia of the Alzheimer type respectively).

Molecular biological techniques have revealed the existence of several subtypes of the dopamine receptor. The dopamine $D_1$ receptor subtype has been shown to occur in at least two discrete forms. Two forms of the $D_2$ receptor subtype, and at least one form of the $D_3$ receptor subtype, have also been discovered. More recently, the $D_4$ (Van Tol et al., *Nature (London)*, 1991, 350, 610) and $D_5$ (Sunahara et al., *Nature (London)*, 1991, 350, 614) receptor subtypes have been described.

The compounds in accordance with the present invention, being ligands for dopamine receptor subtypes within the body, are accordingly of use in the treatment and/or prevention of disorders of the dopamine system.

The present invention accordingly provides a compound of formula I, or a salt thereof or a prodrug thereof:

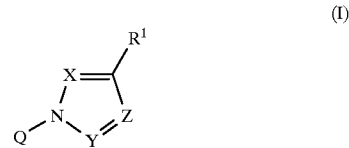

wherein

X represents nitrogen or C—$R^2$;

Y=Z represents a moiety of formula N=C—$R^3$, N=N or CH=N;

Q represents a substituted five-, six- or seven-membered monocyclic heteroaliphatic ring which contains one nitrogen atom as the sole heteroatom and is linked to the five-membered heteroaromatic ring containing the variables X, Y and Z via a carbon atom; and one of $R^1$, $R^2$ and $R^3$ represents $C_{3-7}$ cycloalkyl or a group of formula (i), (ii) or (iii); and the other(s) of $R^1$, $R^2$ and $R^3$, when present in the molecule, independently represent(s) hydrogen or $C_{1-6}$ alkyl; the groups of formula (i), (ii) and (iii) being defined as follows:

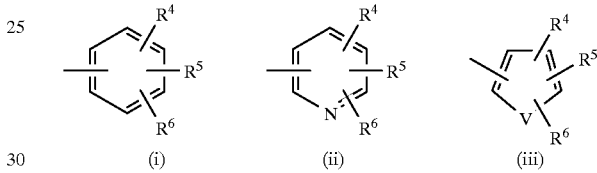

in which V represents oxygen, sulphur or NH;

$R^4$, $R^5$ and $R^6$ independently represent hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$; and $R^a$ and $R^b$ independently represent hydrogen, hydrocarbon or a heterocyclic group.

The monocyclic heteroaliphatic ring Q in the compounds of formula I above represents a substituted pyrrolidinyl, piperidinyl or homopiperidinyl moiety linked through carbon. Examples of suitable rings include the moieties of formula Qa to Qf:

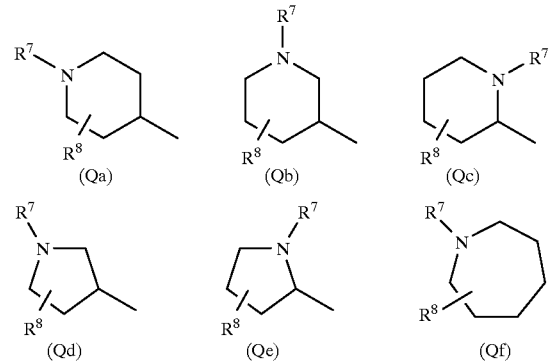

wherein one of $R^7$ and $R^8$ represents hydrocarbon or a heterocyclic group, and the other of $R^7$ and $R^8$ represents hydrogen, hydrocarbon or a heterocyclic group.

A particular monocyclic heteroaliphatic ring represented by the substituent Q in formula I is the ring of structure Qa above.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl and aryl($C_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl and heteroaryl($C_{1-6}$)alkyl groups.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl and t-butyl.

Suitable alkenyl groups include straight-chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Particular aryl groups include phenyl and naphthyl.

Particular aryl($C_{1-6}$)alkyl groups include benzyl, naphthylmethyl, phenethyl and phenylpropyl.

Suitable heterocycloalkyl groups include azetidinyl, pyrrolidinyl, piperidinyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, dibenzofuryl, thienyl, benzthienyl, imidazolyl, oxadiazolyl and thiadiazolyl groups.

Particular heteroaryl($C_{1-6}$)alkyl groups include pyridylmethyl and pyrazinylmethyl.

The hydrocarbon and heterocyclic groups may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, —NR$^v$R$^w$, —NR$^v$COR$^w$, —NR$^v$CO$_2$R$^w$, —NR$^v$SO$_2$R$^w$, —CH$_2$NR$^v$SO$_2$R$^w$, —NHCONR$^v$R$^w$, —CONR$^v$R$^w$, —SO$_2$NR$^v$R$^w$ and —CH$_2$SO$_2$NR$^v$R$^w$, in which R$^v$ and R$^w$ independently represent hydrogen, $C_{1-6}$ alkyl, aryl or aryl($C_{1-6}$)alkyl.

The term "halogen" as used herein includes fluorine, chlorine, bromine and iodine, especially chlorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs,* ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Suitably, one of $R^1$, $R^2$ and $R^3$ represents a group of formula (i) as defined above; and the other(s) of $R^1$, $R^2$ and $R^3$, when present in the molecule, are independently selected from hydrogen and methyl.

In a particular embodiment, the substituents $R^1$, $R^2$ and $R^3$ are independently selected from hydrogen, methyl and phenyl, provided that one, and one only, of $R^1$, $R^2$ and $R^3$ is phenyl.

Suitably, V is oxygen or sulphur.

Suitable values for the substituents $R^4$, $R^5$ and $R^6$ include hydrogen, halogen, trifluoromethyl, cyano, nitro, amino, $C_{1-6}$ alkylamino, di($C_{1-6}$)alkylamino, $C_{1-6}$ alkyl, $C_{1-6}$ alkoxy, aryl($C_{1-6}$)alkoxy and $C_{2-6}$ alkylcarbonyl. Particular values include hydrogen, methyl, ethyl, isopropyl, methoxy, benzyloxy, fluoro and chloro, especially hydrogen.

Suitable values for the substituents $R^7$ and $R^8$ include $C_{2-6}$ alkenyl, $C_{3-7}$ cycloalkyl($C_{1-6}$)alkyl, aryl and aryl($C_{1-6}$)alkyl, any of which groups may be optionally substituted. In addition, one of $R^7$ and/or $R^8$ may represent hydrogen. Examples of suitable substituents on the groups $R^7$ and/or $R^8$ include $C_{1-6}$ alkyl, halogen, trifluoromethyl, $C_{1-6}$ alkoxy, $C_{1-3}$ alkylenedioxy, cyano and nitro.

Particular values of $R^7$ and $R^8$ include hydrogen, allyl, cyclopropylmethyl, cydohexylmethyl, benzyl, methylbenzyl, chlorobenzyl, bromobenzyl, iodobenzyl, dichlorobenzyl, methoxy-benzyl, trifluoromethyl-benzyl, methylenedioxy-benzyl, cyanobenzyl, nitro-benzyl, naphthylmethyl, phenethyl and phenylpropyl, provided that at least one of $R^7$ and $R^8$ is other than hydrogen. Suitably, one of $R^7$ and $R^8$ represents hydrogen, and the other of $R^7$ and $R^8$ is other than hydrogen. Preferably, $R^8$ represents hydrogen and $R^7$ is other than hydrogen.

In a particular embodiment, $R^8$ is hydrogen and $R^7$ represents benzyl, chlorobenzyl or cyanobenzyl.

A particular sub-class of compounds according to the invention is represented by the compounds of formula IIA, and salts and prodrugs thereof:

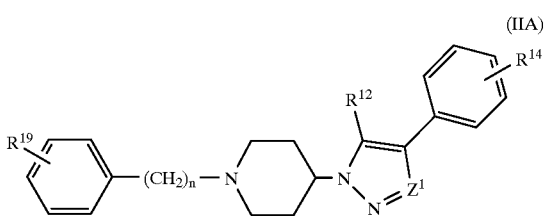

wherein n is zero, 1, 2 or 3, preferably 1;

$Z^1$ represents nitrogen or $C—R^{13}$;

$R^{12}$ and $R^{13}$ independently represent hydrogen or $C_{1-6}$ alkyl; and $R^{14}$ and $R^{19}$ independently represent hydrogen, halogen, trifluoromethyl, cyano, nitro, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl.

Suitably, $R^{12}$ and $R^{13}$ independently represent hydrogen or methyl.

Particular values of $R^{14}$ include hydrogen, fluoro, chloro, methyl, ethyl, methoxy and benzyloxy, especially hydrogen.

Particular values of $R^{19}$ include hydrogen, methyl, ethyl, chloro, bromo, iodo, trifluoromethyl, methoxy, ethoxy, cyano, nitro and dimethylamino, especially hydrogen, chloro or cyano.

Another sub-class of compounds according to the invention is represented by the compounds of formula IIB, and salts and prodrugs thereof:

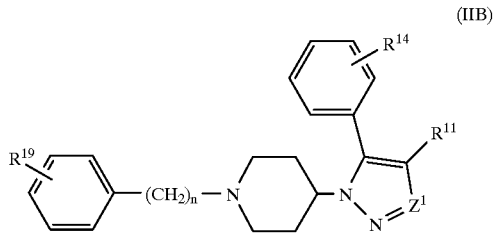

wherein n, $Z^1$, $R^{14}$ and $R^{19}$ are as defined with reference to formula IIA above; and $R^{11}$ represents hydrogen or $C_{1-6}$ alkyl.

Suitably, $R^{11}$ represents hydrogen or methyl.

A further sub-class of compounds according to the invention is represented by the compounds of formula IIC, and salts and prodrugs thereof:

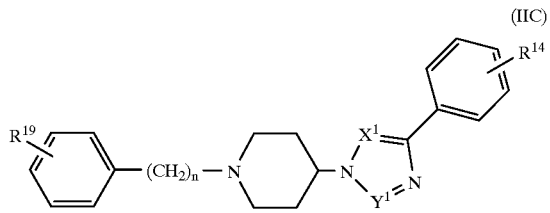

wherein $X^1$ represents nitrogen or $C—R^{12}$;

$Y^1$ represents nitrogen or CH; and n, $R^{12}$, $R^{14}$ and $R^{19}$ are as defined with reference to formula IIA above.

Specific compounds within the scope of the present invention include:

1-benzyl-4-(5-methyl-4-phenylpyrazol-1-yl)piperidine;
1-(3-cyanobenzyl)-4-(5-methyl-4-phenylpyrazol-1-yl) piperidine;
1-(3-chlorobenzyl)-4-(5-methyl-4-phenylpyrazol-1-yl) piperidine;
1-benzyl-4-(3-methyl-4-phenylpyrazol-1-yl)piperidine;
1-(3-cyanobenzyl)-4-(3-methyl-4-phenylpyrazol-1-yl) piperidine;
1-(3-chlorobenzyl)-4-(3-methyl-4-phenylpyrazol-1-yl) piperidine;
1-benzyl-4-(5-methyl-4-phenyl-1,2,3-triazol-1-yl) piperidine;
1-(3-cyanobenzyl)-4-(5-methyl-4-phenyl-1,2,3-triazol-1-yl)piperidine;
1-benzyl-4-(4-methyl-5-phenyl-1,2,3-triazol-1-yl) piperidine;
1-(3-cyanobenzyl)-4-(4-methyl-5-phenyl-1,2,3-triazol-1-yl)piperidine;
1-benzyl-4-(5-phenyltetrazol-2-yl)piperidine;
1-benzyl-4-(4-phenyl-1,2,3-triazol-1-yl)piperidine;
1-benzyl-4-(4-phenylimidazol-1-yl)piperidine;
1-benzyl-4-(5-phenylpyrazol-1-yl)piperidine;
and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Favoured unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of schizophrenia, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III with the anion of a compound of formula IV:

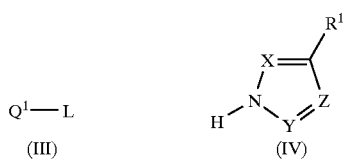

wherein X, Y, Z and $R^1$ are as defined above, $Q^1$ corresponds to the moiety Q as defined above or represents a precursor thereto protected on the nitrogen atom, and L represents a suitable leaving group; followed, if necessary, by separation of the resulting mixture of isomers by conventional means; followed in turn, where necessary, by removal of the N-protecting group from the moiety $Q^1$; and subsequently, if required, attachment to the nitrogen atom thereby deprotected of an appropriate substituent by standard means to afford a product containing the desired moiety Q.

Where $Q^1$ in compound III above represents a precursor to the moiety Q protected on the nitrogen atom, this may be a moiety corresponding to those of formula Qa to Qe as defined above, in which $R^7$ represents an N-protecting group and $R^8$ is hydrogen. Once the reaction between compounds III and IV is complete, the N-protecting group must be removed, and the desired group $R^7$ subsequently attached, by conventional methods.

Where the substituent $Q^1$ represents a precursor to the moiety Q protected on the nitrogen atom, the N-protecting group is suitably an alkoxycarbonyl moiety such as t-butoxycarbonyl (BOC), in which case the N-protecting group can conveniently be removed subsequently as necessary by treatment under acidic conditions, e.g. stirring in trifluoroacetic acid or HCl/ether, optionally in the presence of methanol.

The leaving group L is suitably a halogen atom, e.g. chlorine or bromine; or an alkylsulphonyloxy or arylsulphonyloxy group such as methanesulphonyloxy (mesyloxy) or p-toluenesulphonyloxy (tosyloxy).

The anion of the compound of formula IV may conveniently be generated by treating compound IV with sodium hydride, typically using N,N-dimethylformamide as solvent.

The reaction between compound III and the anion of compound IV is conveniently carried out in a solvent such as N,N-dimethylformamide, typically at the reflux temperature of the solvent.

As indicated above, the reaction between compounds III and IV will often give rise to a mixture of isomeric products of formula I. For example, where the compound of formula IV above is a pyrazole derivative, i.e. a compound wherein X is C—$R^2$, Y is nitrogen and Z is C—$R^3$, and $R^2$ and $R^3$ are different, the reaction is likely to give rise to a mixture of isomers of formula I, one of which corresponds to structure IV as drawn wherein H is replaced by Q, and in the other of which the X and Z moieties are reversed. For this reason, it will generally be necessary to separate the mixture of isomers obtained from the reaction by conventional techniques such as column chromatography.

The 1,2,3-triazol-1-yl derivatives according to the present invention—i.e. the compounds of formula I above wherein X is C—$R^2$ and Y and Z are both nitrogen—may be prepared by a process which comprises reacting an azide derivative of formula V with an alkyne of formula VI:

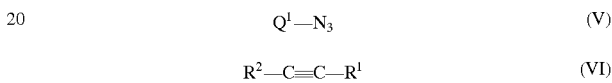

wherein $R^1$, $R^2$ and $Q^1$ are as defined above; followed, if necessary, by separation of the resulting mixture of isomers by conventional means; followed in turn, where necessary, by removal of the N-protecting group from the moiety $Q^1$; and subsequently, if required, attachment to the nitrogen atom thereby deprotected of an appropriate substituent by standard means to afford a product containing the desired moiety Q.

The reaction between compounds V and VI is conveniently carried out by heating the reagents in an inert solvent such as toluene or mesitylene, advantageously at the reflux temperature of the solvent.

Where $R^1$ and $R^2$ are different, the reaction between compounds V and VI is likely to give rise to a mixture of isomeric products in which the $R^1$ and $R^2$ substituents are interchanged. As with those from the reaction between compounds III and IV, the mixture of isomers obtained from the reaction between compounds V and VI can be separated by conventional techniques such as column chromatography.

The pyrazolyl derivatives according to the present invention—i.e. the compounds of formula I above wherein X is C—$R^2$ and Y=Z represents a group of formula N=C—$R^3$—may also be prepared by a process which comprises reacting a hydrazine derivative of formula VII with a compound of formula VIII:

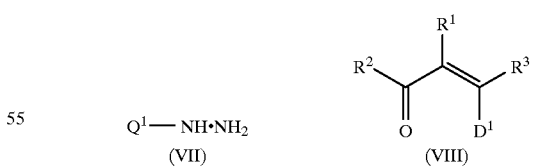

wherein $R^1$, $R^2$, $R^3$ and $Q^1$ are as defined above, and $D^1$ represents a readily displaceable group; followed, if necessary, by separation of the resulting mixture of isomers by conventional means; followed in turn, where necessary, by removal of the N-protecting group from the moiety $Q^1$; and subsequently, if required, attachment to the nitrogen atom thereby deprotected of an appropriate substituent by standard means to afford a product containing the desired moiety Q.

The readily displaceable group $D^1$ is suitably the amine residue of an enamine moiety, e.g. a $C_{1-6}$ alkylamino group such as methylamino.

The reaction between compounds VII and VIII is conveniently carried out in a solvent such as N,N-dimethylformamide, typically at a temperature in the region of 120° C.

In view of the unsymmetrical nature of reactant VIII, the reaction between compounds VII and VIII is likely to give rise to a mixture of isomeric products in which the $R^2$ and $R^3$ substituents are interchanged. As before, the mixture of isomers obtained from this reaction can be separated by conventional techniques such as column chromatography.

The method whereby the group $R^7$ may be attached to the product obtained from any of the above-described processes will suitably comprise a standard carbon-nitrogen bond-forming reaction known from the art, such as N-alkylation. By way of illustration, a compound wherein $R^7$ is hydrogen initially obtained may conveniently be N-benzylated by treatment with a benzyl halide, e.g. benzyl bromide, typically under basic conditions, e.g. using ethyldiisopropylamine in a solvent such as N,N-dimethylformamide, to afford a product wherein $R^7$ is benzyl.

Where they are not commercially available, the starting materials of formula III, IV, V, VI, VII and VIII may be prepared by procedures analogous to those described in the accompanying Examples, or by standard methods well known from the art.

It will be appreciated that any compound of formula I initially obtained from any of the above processes may, where appropriate, subsequently be elaborated into a further desired compound of formula I using techniques known from the art.

In particular, a compound of formula I wherein Q represents a five-, six- or seven-membered aza-aliphatic ring substituted on the sole ring nitrogen atom by a benzyl group initially obtained may be converted into a further compound of formula I wherein Q is substituted on the ring nitrogen atom by a group other than benzyl by a stepwise procedure which comprises removal of the benzyl group followed by attachment of the ring nitrogen substituent by conventional methods. Removal of the benzyl group is conveniently effected by treatment with 1-chloroethyl chloroformate, followed by heating in methanol. Attachment of a substituent to the debenzylated ring nitrogen atom can then be effected, in the case of an alkyl or substituted-alkyl substituent, by reaction with an alkyl halide, typically under basic conditions, e.g. in the presence of ethyldiisopropylamine (Hünig's base), in a suitable solvent such as N,N-dimethylformamide; or under reductive amination conditions, whereby the appropriate aldehyde is reacted with the debenzylated amine in the presence of a reducing agent such as sodium cyanoborohydride.

Where the above-described processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds useful in this invention potently inhibit [$^3$H]-spiperone binding to human dopamine $D_4$ receptor subtypes expressed in clonal cell lines.

[$^3$H]-Spiperone Binding Studies

Clonal cell lines expressing the human dopamine $D_4$ receptor subtype were harvested in PBS and then lysed in 10 mM Tris-HCl pH 7.4 buffer containing 5 mM $MgSO_4$ for 20 min on ice. Membranes were centrifuged at 50,000 g for 15 min at 4° C. and the resulting pellets resuspended in assay buffer (50 mM Tris-HCl pH 7.4 containing 5 mM EDTA, 1.5 mM $CaCl_2$, 5 mM $MgCl_2$, 5 mM KCl, 120 mM NaCl, and 0.1% ascorbic acid) at 20 mg/ml wet weight. Incubations were carried out for 60 min at room temperature (22° C.) in the presence of 0.05–2 nM [$^3$H]-spiperone or 0.2 nM for displacement studies and were initiated by addition of 20–100 μg protein in a final assay volume of 0.5 ml. The incubation was terminated by rapid filtration over GF/B filters presoaked in 0.3% PEI and washed with 10 ml ice-cold 50 mM Tris-HCl, pH 7.4. Specific binding was determined by 10 μM apomorphine and radioactivity determined by counting in a LKB beta counter. Binding parameters were determined by non-linear least squares regression analysis, from which the inhibition constant $K_i$ could be calculated for each test compound.

The compounds of the accompanying Examples were tested in the above assay, and all were found to possess a $K_i$ value for displacement of [$^3$H]-spiperone from the human dopamine $D_4$ receptor subtype of below 1.5 μM.

EXAMPLE 1

1-Benzyl-4-((5-methyl-4-phenyl)pyrazol-1-yl) piperidine dihydrochloride a) N-$^t$Butyloxycarbonyl-4-hydroxypiperidine To a solution of 4-hydroxypiperidine (50 g, 0.5 Mol) in dichloromethane (300 ml) was added $^t$butylcarbonate (129.5 g, 0.6 Mol) in dichloromethane (100 ml) over 0.5 hrs. The mixture was stirred at room temperature for 18 hrs. N,N-Dimethylethylenediamine (16 ml, 0.15 Mol) was added and stirred for 0.5 hrs. The reaction mixture was washed with citric acid (2×100 ml, 1 Mol), water (1×100 ml), saturated sodium bicarbonate (2×100 ml), dried over magnesium sulphate, filtered and concentrated under vacuum to give a colourless oil which went solid on standing (98.5 g), Mp. 59–62° C.

b) N-$^t$Butyloxycarbonyl-4-methylsulphonyloxypiperidine

To a solution of N-$^t$butyloxycarbonyl-4-hydroxypiperidine (10 g, 0.05 Mol) in dichloromethane (60 ml) was added pyridine (4.98 ml, 0.06 Mol), methanesulphonyl chloride (4.6 ml, 0.06 Mol) and a catalytic amount of dimethylaminopyridine. The solution was stirred for 18 hrs., washed with water (2×50 ml), citric acid (1×50 ml, 1 Mol), saturated sodium bicarbonate, dried over magnesium sulphate, filtered and concentrated under vacuum to give a white solid which was triturated with 1:1 diethyl ether and hexane (30 ml) to give the required product, Mp. 92–94° C.

c) N-'Butyloxycarbonyl-4-(1-(3-methyl-4-phenyl) pyrazolyl)piperidine and N-'Butyloxycarbonyl-4-(1-(5-methyl-4-phenyl)pyrazolyl)piperidine To a solution of N-'Butyloxycarbonyl-4-methylsulphonyloxypiperidine (1 g, 0.004 Mol) in N,N-dimethylformamide (20 ml), under nitrogen at room temperature, was added the preformed sodium salt of 3 methyl-4-phenylpyrazole (2.1 g, 0.012 Mol) (formed by addition of sodium hydride to a solution of 3-methyl-4-phenylpyrazole in N,N-dimethylformamide and the resultant solid filtered and dried). The solution was heated to reflux for 2 hrs., left to cool, concentrated under vacuum and the residue was partitioned between dichloromethene (2×50 ml) and water (50 ml). The combined organic layers were washed with brine (2×50 ml), dried (MgSO$_4$), filtered and concentrated under vacuum. The residue was purified by flash silica chromatography using ethyl acetate-hexane (0–40%) as the eluent to give the less polar (0.29 g) and more polar (0.37 g) products. Less polar $^1$H NMR (DMSO) δ 1.43 (9H,s), 1.85 (4H,m), 2.39 (3H,s), 2.94 (2H,m), 4.04 (2H,m), 4.41 (1H,m), 7.23 (1H,m), 7.38 (4H,m), 7.60 (1H, s). More polar $^1$H NMR (DMSO) δ 1.42 (9H,s), 1.75 (2H,m), 1.99 (2H,m), 2.29 (3H,s), 2.90 (2H,m), 4.02 (2H, m), 4.26 (1H,m), 7.21 (1H,m), 7.38 (4H,m), 7.98 (1H,s).

d) 4-((5-Methyl-4-phenyl)pyrazol-1-yl)piperidine hydrochloride

To a solution of the less polar product from Example 1 part c (0.28 g) in diethyl ether (20 ml) was added a solution of hydrogen chloride in ether (30 ml of ~5 Mol). After 2 hrs the solid was filtered and dried to give the title compound (0.22 g). $^1$H NMR (DMSO) δ 2.02 (2H,m), 2.75 (2H,m), 2.41 (3H,s), 3.08 (2H,m), 3.40 (2H,m), 4.58 (1H,m), 7.26 (1H,m), 7.38 (4H,m), 7.64 (1H,s), 9.02 (1H,bs), 9.38 (1H, bs). The structure was confirmed by N.O.E.'s between the 5-methyl protons and the 4-piperidine proton.

e) 1-Benzyl-4-((5-methyl-4-phenyl)pyrazol-1-yl)-piperidine dihydrochloride

To a solution of 4-((5-Methyl-4-phenyl)pyrazol-1-yl)-piperidine hydrochloride (0.21 g, 0.76 mmol) in N,N-dimethylformamide (10 ml) was added benzyl bromide (0.108 ml, 0.91 mmol) and ethyldiisopropylamine (0.46 ml, 2.57 mmol) and the reaction mixture was stirred at 45° C. for 18 hrs. The reaction mixture was concentrated under vacuum and the residue was partitioned between dichloromethane (2×50 ml) and water (50 ml). The combined organic layers were washed with brine (2×50 ml), dried (MgSO$_4$), filtered and concentrated under vacuum. The residue was dissolved in a mixture of diethyl ether and methanol (10 ml, 1:1) and a solution of hydrogen chloride in ether (3 ml ~5 mol) added, after 5 mins. concentrated under vacuum. The residue was recrystallised from ethyl acetate-methanol to give the required compound as a white solid (0.11 g). Mp 198–201° C. $^1$H NMR (DMSO+NaOD) δ 1.82 (2H,m), 2.12 (4H,m), 2.37 (3H,m), 2.91 (2H,m), 3.53 (2H, s), 4.17 (1H,m), 7.34 (10H,m),7.59 (1H,s). MS (CI) m/e 332 [MH]$^+$. Anal. Found C, 64.83; H, 6.71; N, 10.17. C$_{22}$H$_{25}$N$_3$.2HCl.0.2H$_2$O requires C,64.77; H, 6.77; N, 10.17%.

EXAMPLE 2

1-(3-Cyanobenzyl-4-((5-methyl-4-phenyl)pyrazol-1-yl)piperidine

This compound was prepared using the procedure described in Example 1 part e, using 3-cyanobenzyl bromide instead of benzyl bromide, and the free base was recrystallised from ethyl acetate and hexane to give the required compound as a white solid. Mp 145–147° C. dec. $^1$H NMR (DMSO) δ 1.83 (2H,m), 2.1 (2H,m), 2.19 (2H,m), 2.38 (3H,s) 2.90 (2H,m), 3.60 (2H,s), 4.18 (1H,m), 7.24 (1H,m), 7.30 (4H,m), 7.55 (2H,m), 7.59 (2H,m), 7.77 (1H,s). MS (CI) m/e 357 [MH]$^+$. Anal. Found C, 77.36; H, 6.83; N, 15.52. C$_{23}$H$_{24}$N$_4$ requires C,77.50; H, 6.79; N, 15.72%.

EXAMPLE 3

1-(3-Chlorobenzyl)-4-((5-methyl-4-phenyl)pyrazol-1-yl)piperidine

This compound was prepared using the procedure described in Example 1 part e, using 3-chlorobenzyl bromide instead of benzyl bromide, and the free base was recrystallised from ethyl acetate and hexane to give the required compound as a white solid. Mp 126–127° C. $^1$H NMR (DMSO) δ 1.83 (2H,m), 2.10 (4H,m), 2.37 (3H,s), 2.91 (2H,m), 3.55 (2H,s), 4.18 (1H,m), 7.21–7.39 (9H,m), 7.59 (1H,s). MS (CI) m/e 366.5 [MH]$^+$. Anal. Found C, 71.73; H, 6.45; N, 11.55. C$_{22}$H$_{24}$ClN$_3$.0.1H$_2$O requires C,71.86; H, 6.63; N, 11.43%.

EXAMPLE 4

1-Benzyl-4-((3-methyl-4-phenyl)pyrazol-1-yl) piperidine dihydrochloride a) 4-((3-Methyl-4-phenyl)pyrazol-1-yl)piperidine hydrochloride To a solution of the more polar product from Example 1 part c (0.36 g) in diethyl ether (20 ml) was added a solution of hydrogen chloride in ether (30 ml of ~5 Mol). After 2 hrs the solid was filtered and dried to give the title compound (0.33 g). $^1$H NMR (DMSO) δ 2.19 (4H,m), 2.31 (3H,s), 3.06 (2H,m), 3.39 (2H,m), 4.42 (1H,m), 7.23 (1H,m), 7.40 (4H, m) 7.96 (1H,s), 9.09 (1H,bs), 9.34 (1H,bs). The structure was confirmed by N.O.E.'s. between the pyrazole-5-proton and the piperidine-4-proton.

b) 1-Benzyl-4-((3-methyl-4-phenyl)pyrazol-1-yl)piperidine dihydrochloride

To a solution of 4-((3-Methyl-4-phenyl)pyrazol-1-yl) piperidine hydrochloride (0.33 g, 1.19 mmol) in N,N-dimethylformamide (10 ml) was added benzyl bromide (0.17 ml, 1.43 mmol) and ethyldiisopropylamine (0.70 ml, 4.05 mmol) and the reaction mixture was stirred at 45° C. for 18 hrs. The reaction mixture was concentrated under vacuum and the residue was partitioned between dichloromethane (2×50 ml) and water (50 ml). The combined organic layers were washed with brine (2×50 ml), dried (MgSO$_4$), filtered and concentrated under vacuum. The residue was dissolved in a mixture of diethyl ether and methanol (10 ml, 1:1) and a solution of hydrogen chloride in ether (3 ml ~5 mol) added, after 5 mins. concentrated under vacuum. The residue was recrystallised from ethyl acetate-methanol to give the required compound as a white solid (0.22 g). Mp 194–195° C. $^1$H NMR (DMSO+NaOD) δ 1.98 (4H,m), 2.09 (2H,m), 2.30 (3H,s), 2.91 (2H,m), 3.73 (2H,s), 4.07 (1H,m), 7.21–7.44 (10H,m), 7.96 (1H,s). MS (CI) m/e 332 [MH]$^+$. Anal. Found C, 64.98; H, 6.84; N, 10.24. C$_{22}$H$_{25}$N$_3$.2HCl.0.2H$_2$O requires C,64.77; H, 6.77; N, 10.17%.

EXAMPLE 5

1-(3-Cyanobenzyl)-4-((3-methyl-4-phenyl)pyrazol-1-yl)piperidine oxalate

This compound was prepared using the procedure described in Example 4, using 3-cyanobenzyl bromide instead of benzyl bromide, and the free base was converted into its oxalate salt before being recrystallised from ethyl acetate and methanol to give the required compound as a white solid. Mp 142–144° C. $^1$H NMR (DMSO+NaOD) δ 2.10 (4H,bs), 2.30 (3H,s), 2.50 (2H,m), 3.12 (2H,m), 3.94 (2H,s), 4.22 (1H,m), 7.20–7.80 (9H,m), 9.98 (1H,s). MS (CI) m/e 357 [MH]$^+$. Anal. Found C, 66.46; H, 5.69; N, 12.40. $C_{23}H_{24}N_4.C_2H_2O_4.0.2H_2O$ requires C, 66.71; H, 5.91; N, 12.45%.

EXAMPLE 6

1-(3-Chlorobenzyl)-4-((3-methyl-4-phenyl)pyrazol-1-yl)piperidine oxalate

This compound was prepared using the procedure described in Example 4, using 3-chlorobenzyl bromide instead of benzyl bromide, and the free base was converted into its oxalate salt before being recrystallised from ethyl acetate and methanol to give the required compound as a white solid. Mp 178–180° C. $^1$H NMR (DMSO) δ 2.11 (4H,m), 2.30 (3H,s), 2.62 (2H,m) 3.14 (2H,m), 3.90 (2H,s), 4.23 (1H,m), 7.20–7.52 (9H,m), 7.98 (1H,s). MS (CI) m/e 365 [MH]$^+$. Anal. Found C, 63.33; H, 5.70; N, 9.18. $C_{22}H_{24}ClN_2.C_2H_2O_4$ requires C, 63.22; H, 5.75; N, 9.22%.

EXAMPLE 7 and EXAMPLE 9

1-Benzyl-4-((4-methyl-5-phenyl)triazol-1-yl)piperidine dihydrochloride and 1-Benzyl-4-((5-methyl-4-phenyl)triazol-1-yl)piperidine dihydrochloride a) N-$^t$Butyloxycarbonyl-4-bromopiperidine To a solution of N-$^t$butyloxycarbonyl-4-hydroxypiperidine (20 g, 0.1 Mol) in tetrahydrofuran (200 ml) at 0° C. was added triphenyl phosphine (28.85 g, 0.11 Mol) and carbon tetrabromide (36.48, 0.11 Mol), the reaction mixture was allowed to warm to room temperature, then stirred for 2 hrs. The mixture was filtered and concentrated under vacuum. The residue was purified by flash silica chromatography using dichloromethanehexane (10–60%) as the eluent to give the required product (21.5 g). $^1$H NMR (CDCl$_3$) δ 1.48 (9H,s), 1.95(2H,m), 2.06 (2H,m), 3.26 (2H,m), 3.65 (2H,m), 4.32 (1H,m).

b) 4-Azido-N-$^t$butyloxycarbonylpiperidine

To a solution of N-$^t$butyloxycarbonyl-4-bromopiperidine (8.8 g, 33.5 mmol) in N,N-dimethylformamide (50 ml) was added sodium azide (6.5 g, 100.4 mmol) and the reaction mixture was heated at 60° C. for 18 hrs., cooled to room temperature, poured into water (200 ml) and extracted with dichloromethane (2×200 ml). The combined organic layers were washed with brine (2×50 ml), dried (MgSO$_4$), filtered and concentrated under vacuum, to give the required product (6.0 g). $^1$H NMR (CDCl$_3$) δ 1.28 (9H, s), 1.56 (2H,m), 1.88 (2H,m), 3.10 (2H,m), 3.58 (1H,m), 3.82 (2H,m).

c) N-$^t$Butyloxycarbonyl-4-((4-methyl-5-phenyl)triazol-1-yl)piperidine and N-$^t$Butyloxycarbonyl-4-((5-methyl-4-phenyl)triazol-1-yl)piperidine To a solution of 4-azido-N-$^t$butyloxycarbonylpiperidine (2.5 g, 9.5 mmol) in mesitylene (20 ml) was added phenylpropyne (15 ml, 27 mmol) and the mixture was heated to reflux under nitrogen for 24 hrs. After cooling the crude reaction mixture was purified by flash silica chromatography to give a mixture of the isomers in a ratio of 2:1 (1.39 g). $^1$H NMR (CDCl$_3$) δ 1.40 (9H,s, major isomer), 1.44 (9H,s, minor isomer), 1.95 (4H,m, minor+major isomer), 2.17 (3H,s, minor+major isomer), 2.81 (2H,m, major isomer) 2.99 (2H,m, minor isomer), 3.98 (2H,m, major isomer), 4.09 (2H,m, minor isomer), 4.33 (1H,m, major isomer), 4.61 (1H,m, minor isomer), 7.29–7.69 (5H,m, minor+major isomer).

d) 4-((4-Methyl-5-phenyl)triazol-1-yl)piperidine and 4-((5-Methyl-4-phenyl)triazol-1-yl)piperidine To a solution of the mixture of N-$^t$butyloxycarbonyl-4-((4-methyl-5-phenyl)triazol-1-yl)piperidine and N-$^t$butyloxycarbonyl-4-((5-methyl-4-phenyl)triazol-1-yl)piperidine (1.2 g, 3.3 mmol) in methanol (30 ml) was added hydrogen chloride in methanol (300 ml, ~5 Mol). The reaction mixture was stirred at room temperature for 18 hrs. The solvent was removed by evaporation and the solid was triturated with diethyl ether to give the product as a mixture of isomers (0.59 g). $^1$H NMR (DMSO+NaOD) δ 1.85 (2H,m, major isomer), 1.96 (2H,m, minor isomer), 2.17 (3H,s, major and minor isomer), 2.24 (2H,m, major and minor isomer), 2.96 (2H,m, major isomer), 3.06 (2H,m, minor isomer), 3.79 (2H,m, major and minor isomer), 4.17 (1H,m, major isomer), 4.43 (1H,m, minor isomer), 7.39–7.68 (5H,m,major and minor isomer).

e) 1-Benzyl-4-((4-methyl-5-phenyl)triazol-1-yl)piperidine and 1-Benzyl-4-((5-methyl-4-phenyl)triazol-1-yl)piperidine dihydrochloride To a solution of a mixture of 4-((4-methyl-5-phenyl)triazol-1-yl)piperidine and 4-((5-methyl-4-phenyl)triazol-1-yl)piperidine (0.75 g, 3.1 mmol) in N,N-dimethylformamide (50 ml) was added benzyl bromide (0.41 ml, 3.41 mmol) and ethyldiisopropylamine (0.81, 4.5 mmol). The reaction mixture was stirred at room temperature for 18 hrs. Then poured into sodium hydroxide (200 ml, 1 Mol) and extracted with dichloromethane (2×200 ml). The combined organic layers were washed with water (4×50 ml), brine (2×50 ml), dried (MgSO$_4$), filtered and concentrated under vacuum, to give the required product as a mixture of isomers. These were separated using chromatography to give the less polar product, 1-benzyl-4-((5-methyl-4-phenyl)triazol-1-yl)piperidine (109 mg), and the more polar product, 1-benzyl-4-((4-methyl-5-phenyl)triazol-1-yl)piperidine (200 mg); these structures were verified by NOE studies. The less polar isomer was recrystallised as its free base using ethyl acetate and hexane to give 1-benzyl-4-((5-methyl-4-phenyl)triazol-1-yl)piperidine (Example 7) (21 mg). Mp 178–180° C. $^1$H NMR (DMSO) δ 2.00 (2H,m), 2.17 (4H, m), 2.46 (3H,s), 2.9 (2H,m), 3.55 (2H,s), 4.36 (1H,m), 7.26–7.27 (6H,m), 7.34–7.48 (2H,m), 7.65–7.67 (2H,m). MS (CI) m/e 333 [MH]$^+$. The more polar isomer was converted into its dihydrochloride salt and recrystallised from ethyl acetate and methanol to give 1-benzyl-4-((5-methyl-4-phenyl)triazol-1-yl)piperidine dihydrochloride (Example 9) as a white solid (193 mg). Mp 156° C. $^1$H NMR (DMSO) δ 2.13 (2H,m), 2.17 (3H,s), 2.60 (2H,m), 3.08 (2H,m), 3.38 (2H, m), 4.23 (2H,s), 4.42 (1H,m) 5.76 (2H,bs) 7.43–7.68 (10H, m). MS (CI) m/e 333 [MH]$^+$. Anal. Found C, 57.85; H, 6.80; N, 12.85. $C_{21}H_{24}N_4.2HCl.1.7H_2O$ requires C, 57.90; H, 6.50; N, 12.90%.

EXAMPLE 8

1-(3-Cyanobenzyl)-4-((5-methyl-4-phenyl)triazol-1-yl)piperidine

This compound was prepared using the procedure described in Example 7, part e using 3-cyanobenzyl bromide instead of benzyl bromide to give the less polar isomer, 1-(3-cyanobenzyl)-4-((5-methyl-4-phenyl)triazol-1-yl)piperidine. Mp 210–212° C. $^1$H NMR (DMSO) δ 1.98 (2H,m), 2.17 (4H,m), 2.47 (3H,s), 2.93 (2H,m), 3.63 (2H,s), 4.38 (1H,m), 7.33–7.80 (9H,m). MS (CI) m/e 358 [MH]$^+$.

Anal. Found C, 72.81; H, 6.06; N, 19.05. $C_{22}H_{23}N_5.0.2H_2O$ requires C,73.18; H, 6.53; N, 19.39%.

EXAMPLE 10

1-(3-Cyanobenzyl)-4-((4-methyl-5-phenyl)triazol-1-yl)piperidine

This compound was prepared using the procedure described in Example 7, part e using 3-cyanobenzyl bromide instead of benzyl bromide to give the more polar isomer, 1-(3-cyanobenzyl)-4-((4-methyl-5-phenyl)triazol-1-yl) piperidine. Mp 150° C. $^1$H NMR (DMSO) δ 1.88 (2H,m), 1.98 (2H,m), 2.10 (2H,m), 2.16 (3H,s), 2.88 (2H,m), 3.54 (2H,s), 4.11 (1H,m), 7.40–7.73 (9H,m) MS (CI) m/e 358 [MH]$^+$. Anal. Found C, 73.96; H, 6.50; N, 19.41. $C_{22}H_{23}N_5$ requires C,73.92; H, 6.49; N, 19.59%.

EXAMPLE 11

1-Benzyl-4-((4-phenyl)tetrazol-1-yl)piperidine hydrochloride

This compound was prepared using the procedure described in Example 1 parts c–e, using 5-phenyltetrazole instead of 3-methyl-4-phenylpyrazole and the hydrochloride salt recrystallised from ethyl acetate and methanol to give the required compound as a white solid. Mp 220–223° C. dec. $^1$H NMR (DMSO) δ 2.08–2.29 (6H,m), 2.90 (2H,m), 3.54 (2H,s), 4.90 (1H,m), 7.25 (1H,m), 7.35 (4H,m), 7.58 (3H,m), 8.07 (2H,m). MS (CI) m/e 320 [MH]$^+$. Anal. Found C, 64.27; H, 6.26; N, 19.44. $C_{19}H_{21}N_5.HCl$ requires C, 64.13; H, 6.23; N, 19.68%.

EXAMPLE 12

1-Benzyl-4-((4-phenyl)triazol-1-yl)piperidine a) N-$^t$Butyloxycarbonyl-4-((4-phenyl)triazol-1-yl)piperidine To a solution of 4-azido-N-$^t$butyloxycarbonylpiperidine (2.5 g, 9.5 mmol) in toluene (60 ml) was added phenylacetylene (15 ml, 27 mmol) and the mixture was heated to reflux under nitrogen for 24 hrs. Concentrated under vacuum and the residue was purified by flash silica chromatography using ethyl acetate-hexane (0–70%) as the eluent to give the required product (2.6 g). $^1$H NMR (CDCl$_3$) δ 1.49 (9H,s), 2.07 (4H,m), 2.27 (2H,m), 2.96 (1H,m), 4.39 (2H,m), 7.26–7.85 (6H,m).

b) 1-Benzyl-4-((4-phenyl)triazol-1-yl)piperidine

To a solution of N-$^t$butyloxycarbonyl-4-((4-phenyl)triazol-1-yl)piperidine (2.5 g) in a 1:1 mixture of diethyl ether and methanol (10 ml) was added a solution of hydrogen chloride in methanol (10 ml, ~5 mol) and the reaction mixture was stirred at room temperature for 72 hrs. The solid was filtered off and dried then redissolved in N,N-dimethylformamide (20 ml), to which was added benzyl bromide (0.4 ml, 3.4 mmol) and ethyldiisopropylamine (0.55 ml, 3.4 mmol). The reaction mixture was stirred at room temperature for 18 hrs under nitrogen, then poured into water (200 ml) and extracted with dichloromethane (3×100 ml). The combined organic layers were washed with brine (2×50 ml), dried (MgSO$_4$), filtered and concentrated under vacuum. The residue was purified by flash silica chromatography using methanol in dichloromethane (0–4%) and ammonia (0.5%). The product obtained was redissolved in a 1:1 mixture of diethyl ether and methanol (5 ml) with hydrogen chloride in methanol (10 ml, ~5 mol). After 5 mins the solvent was removed under vacuum and the residue was recrystallized from methanol and ethyl acetate to give the required product as a white solid (85 mg). M.p 206–280° C. $^1$H NMR (DMSO) δ 2.11 (4H,m), 2.60 (2H,m), 2.77 (2H,m), 3.04 (2H,m), 4.52 (1H,m), 7.18–7.85 (11H,m). MS (CI) m/e 319 [MH]$^+$. Anal. Found C, 64.90; H, 6.43; N, 15.05. $C_{20}H_{22}N_4.HCl.0.75H_2O$ requires C, 65.21; H, 6.70; N, 15.21%.

EXAMPLE 13

1-Benzyl-4-((4-phenyl)imidazol-1-yl)piperidine dihydrochloride

This compound was prepared using the procedure described in Example 1 parts c–e, using 4-phenylimidazole instead of 3-methyl-4-phenylpyrazole and the hydrochloride salt was recrystallised from ethyl acetate and methanol to give the required compound as a white solid. Mp 165° C. dec. $^1$H NMR (DMSO+NaOD) δ 1.98 (4H,m), 2.12 (2H,m), 2.90 (2H,m), 3.52 (2H,s), 4.08 (1H,m), 7.19–7.34 (8H,m), 7.74 (4H,m). MS (CI) m/e 318 [MH]$^+$. Anal. Found C, 60.94; H, 6.99; N, 10.08. $C_{21}H_{23}N_3.2HCl. 1.3H_2O$ requires C, 60.96 H, 6.72; N, 10.16%.

EXAMPLE 14

1-Benzyl-4-((5-phenyl)pyrazol-1-yl)piperidine hydrochloride

To a solution of 1-benzyl-4-hydrazinopiperidine (0.2 g, 0.0098 Mol) in dimethylformamide (10 ml) was added 3-(N-methylamino)acrylophenone (0.157 g, 0.0098 Mol) and the reaction mixture was heated at 120° C. for 2 h. The solvent was removed under high vacuum and the residue was purified by chromatography on silica gel using 5% methanol in dichloromethane as eluent. The product was dissolved in methanol (20 ml) that had been presaturated with dry hydrogen chloride and after 5 mins concentrated in vacuo. The solid obtained was recrystallised from methanol-ethyl acetate to give the title compound (0.11 g). Mp. 217–218° C. $^1$H NMR (DMSO) δ 2.04 (2H,m), 2.51 (2H,m), 3.10 (2H,m), 3.36 (2H,m), 4.24 (2H,d, J=5 Hz), 4.41 (1H, m), 6.34 (1H,s), 7.44–7.68 (11H,m), 10.92 (1H,bs). The regiochemistry of this compound was confirmed by observation of N.O.E.'s between the proton at the 4-position of the piperidine (δ 4.41) and the ortho protons of the phenyl ring attached to the pyrazole. MS (CI) m/e 218 [MH]$^+$. Anal. Found C, 67.65; H, 6.90; N, 11.23. $C_{21}H_{23}N_3.HCl.H_2O$ requires C, 67.82; H, 7.05; N, 11.30%.

We claim:

1. A compound of formula I, or a pharmaceutically acceptable salt thereof:

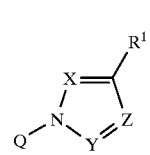

(I)

wherein

X represents C—R$^2$;

Y=Z represents a moiety of formula N=C—R$^3$;

Q represents a moiety of formula Qa, Qb, or Qc:

(Qa) (Qb) (Qc)

one of $R^1$, $R^2$ and $R^3$ represents $C_{3-7}$ cycloalkyl or a group of formula (i), (ii) or (iii); and the others of $R^1$, $R^2$ and $R^3$ independently represent hydrogen or $C_{1-6}$ alkyl; the groups of formula (i), (ii) and (iii) being defined as follows:

(i) (ii) (iii)

in which V represents oxygen, sulphur or NH;

$R^4$, $R^5$ and $R^6$ independently represent hydrogen, methyl, ethyl, isopropyl, methoxy, benzyloxy, fluoro or chloro;

$R^7$ represents benzyl, chlorobenzyl or cyanobenzyl; and $R^8$ represents hydrogen.

2. A compound as claimed in claim 1 represented by formula IIA, or a pharmaceutically acceptable salt thereof:

(IIA)

wherein n is 1;

$Z^1$ represents C—$R^{13}$;

$R^{12}$ and $R^{13}$ independently represent hydrogen or $C_{1-6}$ alkyl;

$R^{14}$ represents hydrogen, fluoro, chloro, methyl, ethyl, methoxy or benzyloxy; and $R^{19}$ represents hydrogen, chloro or cyano.

3. A compound as claimed in claim 1 represented by formula IIB, or a pharmaceutically acceptable salt thereof:

(IIB)

wherein n is 1;

$Z^1$ represents C—$R^{13}$;

$R^{11}$ and $R^{13}$ independently represent hydrogen or $C_{1-6}$ alkyl;

$R^{14}$ represents hydrogen, fluoro, chloro, methyl, ethyl, methoxy or benzyloxy; and $R^{19}$ represents hydrogen, chloro or cyano.

4. A compound as claimed in claim 2 wherein $R^{14}$ represents hydrogen.

5. A compound as claimed in claim 1 selected from:

1-benzyl-4-(5-methyl-4-phenylpyrazol-1-yl)piperidine;

1-(3-cyanobenzyl)-4-(5-methyl-4-phenylpyrazol-1-yl)piperidine;

1-(3-chlorobenzyl)-4-(5-methyl-4-phenylpyrazol-1-yl)piperidine;

1-benzyl-4-(3-methyl-4-phenylpyrazol-1-yl)piperidine;

1-(3-cyanobenzyl)-4-(3-methyl-4-phenylpyrazol-1-yl)piperidine;

1-(3-chlorobenzyl)-4-(3-methyl-4-phenylpyrazol-1-yl)piperidine; and 1-benzyl-4-(5-phenylpyrazol-1-yl)piperidine;

or a pharmaceutically acceptable salt thereof.

6. A pharmaceutical composition comprising an effective amount of a compound as claimed in claim 1 in association with a pharmaceutically acceptable carrier.

7. A compound as claimed in claim 3 wherein $R^{14}$ represents hydrogen.

* * * * *